US006811562B1

United States Patent
Pless

(10) Patent No.: US 6,811,562 B1
(45) Date of Patent: Nov. 2, 2004

(54) PROCEDURES FOR PHOTODYNAMIC CARDIAC ABLATION THERAPY AND DEVICES FOR THOSE PROCEDURES

(75) Inventor: Benjamin D. Pless, Atherton, CA (US)

(73) Assignee: Epicor, Inc., Sunnyvale, CA (US)

( * ) Notice: Subject to any disclaimer, the term of this patent is extended or adjusted under 35 U.S.C. 154(b) by 193 days.

(21) Appl. No.: 09/629,242

(22) Filed: Jul. 31, 2000

(51) Int. Cl.[7] .................................................. A61N 5/06
(52) U.S. Cl. ............................ 607/88; 128/898; 606/13
(58) Field of Search .................... 128/898; 607/88–92; 604/20; 606/2, 10, 13, 14

(56) References Cited

U.S. PATENT DOCUMENTS

| | | | |
|---|---|---|---|
| 5,169,395 A | | 12/1992 | Narciso, Jr. |
| 5,403,308 A | | 4/1995 | Wood et al. |
| 5,671,314 A | | 9/1997 | Gregory et al. |
| 5,824,005 A | | 10/1998 | Motamedi et al. |
| 6,143,019 A | * | 11/2000 | Motamedi et al. .......... 128/898 |
| 6,164,283 A | * | 12/2000 | Lesh ........................... 128/898 |
| 6,195,411 B1 | * | 2/2001 | Dinsmore .................... 378/136 |
| 6,224,566 B1 | * | 5/2001 | Loeb ............................ 604/20 |
| 6,443,974 B1 | * | 9/2002 | Oron et al. ................... 607/88 |
| 2001/0037080 A1 | | 11/2001 | Mueller et al. |
| 2002/0095197 A1 | * | 7/2002 | Lardo et al. .................. 607/89 |

FOREIGN PATENT DOCUMENTS

| WO | WO 92/17243 A2 | 10/1992 |
|---|---|---|
| WO | WO 99/15236 A1 | 4/1999 |

* cited by examiner

*Primary Examiner*—Beverly M. Flanagan
*Assistant Examiner*—Henry M Johnson, III
(74) *Attorney, Agent, or Firm*—Morrison & Foerster LLP

(57) ABSTRACT

This relates to procedures and to devices for treating cardiac tissue by forming lesions in that tissue using photodynamic therapy techniques. In particular, the procedure is valuable for rectifying various cardiac arrhythmias with those so-formed lesions. Central to this procedure is the delivery of light to the desired lesion site in cooperation with delivery of a photodynamic drug to that site. The invention also relates to devices, particularly catheters, that are suitable for delivering the light for forming those lesions.

23 Claims, 5 Drawing Sheets

PROCEDURES FOR PHOTODYNAMIC CARDIAC ABLATION THERAPY AND DEVICES FOR THOSE PROCEDURES

FIELD OF THE INVENTION

This invention relates to procedures and to devices for treating cardiac tissue by forming lesions in that tissue using photodynamic therapy techniques. In particular, the procedure is valuable for rectifying various cardiac arrhythymias with those so-formed lesions. Central to this procedure is the delivery of light to the desired lesion site in cooperation with delivery of a photodynamic drug to that site. The invention also relates to devices, particularly catheters, that are suitable for delivering the light for forming those lesions.

BACKGROUND OF THE INVENTION

Many abnormal medical conditions in humans and other mammals have been associated with disease and other aberrations along the lining or walls of blood vessels. Treatment of such abnormal wall conditions has included various medical device technologies that deliver various forms of energy to specific regions of vascular wall tissue.

For instance, atherosclerosis, a vascular disease characterized by abnormal deposits upon vessel walls or the thickening of those walls, is an example of an abnormal wall condition. The dangers related to flow blockages or functional occlusions resulting from the disease have made atherosclerosis the focus of many medical devices. Such devices are often categorized by structure and tissue treatment mechanism. The categories include direct contact electrode devices, resistance heating devices, light transmission devices, light-to-heat conversion devices, hot fluid devices, and radio frequency (RF) heated devices.

The first category includes a variety of contact electrode devices. For instance, U.S. Pat. No. 4,998,933, to Eggers et al, describes a catheter for thermal angioplasty using a heated electrode in direct contact with surrounding tissue or plaque deposits. The heated electrode serves to treat the diseased lumen walls. U.S. Pat. No. 4,676,258, to Inokuchi et al, and U.S. Pat. No. 4,807,620, to Strul et al, disclose devices designed to treat surrounding tissues using heat generated by two electrodes within the device and an RF power source.

U.S. Pat. No. 4,672,962, to Hershenson, and U.S. Pat. No. 5,035,694, to Kasprzyk et al, disclose devices which may be categorized as resistance heating probes. In each of these devices, current flowing through a conductive material at the end of the device provides heat that is transmitted to surrounding tissues for treatment of atherosclerosis and other diseases. Current is transmitted in each of these devices by electrically conductive materials. In contrast, U.S. Pat. No. 5,226,430, to Spears et al, discloses a device which uses light transmitting fiber to transmit energy to a heat generating element at the tip of the device. That heat generating element in turn transmits heat energy to a surrounding balloon structure which is in contact with surrounding tissue. Similarly, U.S. Pat. No. 4,790,311, to Ruiz, discloses an angioplasty catheter system having heat generating electrode at the tip of the device that is heated using RF energy. This device may be categorized as an RF heated device.

U.S. Pat. Nos. 5,190,540 and 5,292,321, to Lee, describe hot fluid-containing devices. Lee '540 shows a balloon catheter designed for remodeling a body lumen. This catheter uses a multilumen shaft that delivers a heated fluid to an expandable balloon. The expanded balloon heats the tissue that is in contact with the expanded balloon. Lee '321 shows a somewhat similar device. However, the expandable balloon is instead filled with a selected thermoplastic material that becomes softer and more compliant when heated by a heating element.

Diseased or structurally damaged blood vessels often involve various abnormal wall conditions. The inducement of thrombosis and control of hemorrhaging within such vessels have been the focus of several devices that use catheter-based heat sources for cauterizing damaged tissues. U.S. Pat. No. 4,449,528, to Auth et al, discloses a thermal cautery probe designed for heating specific layers of tissue without producing deep tissue damage. The mechanism of heat generation in this device is a resistive coil within the cautery probe that is electrically connected to a power source. U.S. Pat. No. 4,662,368, to Hussein et al, discloses a device designed for localized heat application within a lumen; In this device, energy in the form of light is delivered to the tip of the device for heat generation, by a flexible fiber. Heat from an element that converts light energy to heat energy passes to the adjacent tissue.

Although there are a variety of devices that deliver energy to vascular lumena, none of them deliver the energy in the form of light which cooperatively forms lesions in cardiac tissue using photodynamic chemicals to treat that cardiac tissue and to prevent various forms of fibrillation.

Atrial Fibrillation

Cardiac arrhythmias, and atrial fibrillation in particular, are common, dangerous medical ailments, particularly in the aging population. In patients with normal sinus rhythm, the heart, which is made up of atrial, ventricular, and excitatory conduction tissue, is electrically excited to beat in a synchronous, patterned fashion. In patients with cardiac arrhythmia, regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction generally occurs at various, specific regions of the heart, for example: in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet re-entrant type, characterized by multiple asynchronous loops of electrical impulses that are scattered about the atrial chamber. These arrhythmias are often self propagating. Cardiac arrhythmias may also have a focal origin, such as when an isolated region of tissue in an atrium fires autonomously in a rapid, repetitive fashion. Cardiac arrhythmias, including atrial fibrillation, may be detected using the global technique of an electrocardiogram (EKG). More sensitive procedures of mapping the specific conduction along the cardiac chambers have also been disclosed, such as for example in U.S. Pat. No. 4,641,649 to Walinsky et al and WO 96/32897 to Desai.

A variety of clinical conditions may result from the irregular cardiac function and resulting hemodynamic abnormalities associated with atrial fibrillation, including stroke, heart failure, and other thromboembolic events. Atrial fibrillation is believed to be a significant cause of cerebral stroke; the abnormal hemodynamics in the left atrium caused by the fibrillatory wall motion precipitate the formation of thrombus within the atrial chamber. A thromboembolism is ultimately thrown off into the left ventricle, which then pumps the embolism into the cerebral circulation causing a stroke. For these reasons, there are a number of procedures for treating atrial arrhythmias.

Conventional Atrial Arrhythmia Treatments

There are several pharmacological approaches intended to remedy or otherwise treat atrial arrhythrnias. See, for example, U.S. Pat. No. 4,673,563, to Berne et al; U.S. Pat. No. 4,569,801, to Molloy et al; and Hindricks, et al in "Current Management of Arrhythmias" (1991). However, such pharmacological solutions are not always effective and may in some cases result in proarrhythmia and long term inefficacy.

Several surgical approaches have been developed to treat atrial fibrillation. One example is known as the "maze procedure," as is disclosed by Cox, J. L. et al in "The surgical treatment of atrial fibrillation. I. Summary" *Thoracic and Cardiovascular Surgery* 101(3), pp. 402–405 (1991); and also by Cox, J. L. in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control via a specific pattern of incisions in the tissue wall. Early on, the "maze" procedure included surgical incisions in both the right and the left atrial chambers. However, more recent reports predict that the surgical "maze" procedure may be effective when performed only in the left atrium. See, Sueda et al, "Simple Left Atrial Procedure for Chronic Atrial Fibrillation Associated With Mitral Valve Disease" (1996).

The "maze procedure" as surgically performed in the left atrium generally includes forming vertical incisions from the two superior pulmonary veins and terminating in the region of the mitral valve annulus, traversing the inferior pulmonary veins en route. An additional horizontal incision also connects the superior ends of the two vertical incisions. The atrial wall region bordered by the pulmonary vein ostia is therefore isolated from the other atrial tissue. In this way, the mechanical sectioning of atrial tissue eliminates the precipitating conduction to the atrial arrhythmia by creating conduction blocks within the aberrant electrical conduction pathways.

Although the "maze" procedure is generally effective, it is a highly invasive procedure. Nevertheless, the procedures have provided a guiding principle for alleviating arrhythmia: the mechanical isolation of faulty cardiac tissue often prevents atrial arrhythmia, and particularly atrial fibrillation caused by perpetually wandering reentrant wavelets or focal regions of arrhythmogenic conduction.

Modern Catheter Treatments for Atrial Arrhythmia

Success with surgical interventions through atrial segmentation, particularly with regard to the surgical "maze" procedure just described, has caused others to develop less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as are disclosed in the following: U.S. Pat. No. 5,617,854, to Munsif; U.S. Pat. No. 4,898,591, to Jang et al; U.S. Pat. No. 5,487,385, to Avitall; and U.S. Pat. No. 5,582,609 to Swanson.

Additional examples of catheter-based tissue ablation in performing less-invasive cardiac chamber segmentation procedures are also disclosed in the following articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132–1144 (1996).

Furthermore, various energy delivery modalities (microwave, laser, and more commonly, RF) is used to create conduction blocks (atrial wall lesions) along the cardiac tissue wall. See, WO 93/120767, to Stem et al; U.S. Pat. No. 5,104,393, to Isner et al; and U.S. Pat. No. 5,575,766, to Swartz et al.

Additionally, ablation catheter devices and methods have also been used to ablate arrhythmogenic tissue of the left-sided accessory pathways, such as those associated with the Wolff-Parkinson-White syndrome, through the wall of an adjacent region along the coronary sinus.

For example, Fram et al, in "Feasibility of RF Powered Thermal Balloon Ablation of Atrioventricular Bypass Tracts via the Coronary Sinus: In vivo Canine Studies," *PACE*, Vol. 18, p 1518–1530 (1995), discloses attempted thermal ablation of left-sided accessory pathways in dogs using a balloon which is heated with bipolar radiofrequency electrodes positioned within the balloon. Fram et al suggests that the lesion depth of some population groups may be sufficient to treat patients with Wolff-Parkinson-White syndrome.

Additional examples of cardiac tissue ablation from the region of the coronary sinus for the purpose of treating particular types of cardiac arrhythmias are disclosed in: "Long-term effects of percutaneous laser balloon ablation from the canine coronary sinus", Schuger CD et al., *Circulation* (1992) 86:947–954; and "Percutaneous laser balloon coagulation of accessory pathways", McMath L P et al., Diagn. Ther. Cardiovasc. Interven. 1991; 1425:165–171.

Focal Arrhythmias Originating from Pulmonary Veins

Atrial fibrillation may be focal in nature, caused by the rapid and repetitive firing of an isolated center within the atrial cardiac muscle tissue. These foci, defined by regions exhibiting a concentric pattern of electrical activation, may act either to trigger atrial fibrillation or to sustain the fibrillation. Some studies have suggested that focal arrhythmia often originates from a tissue region along the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways.

One example of a focal ablation method intended to destroy and thereby treat focal arrhythmia originating from a pulmonary vein is disclosed by Haissaguerre et al, "Right and Left Atrial Radiofrequency Catheter Therapy of Paroxysmal Atrial Fibrillation," *Journal of Cardiovascular Electrophysiology* 7(12), pp. 1132–1144 (1996). Haissaguerre et al discloses radiofrequency catheter ablation of drug-refractory paroxysmal atrial fibrillation using linear atrial lesions complemented by focal ablation targeted at arrhythmogenic foci. The site of the arrhythmogenic foci were generally located just inside the superior pulmonary vein.

In another focal ablation example, Jais et al. in "A focal source of atrial fibrillation treated by discrete radiofrequency ablation" *Circulation* 95:572–576 (1997) discusses the use of an RF ablative technique to patients with paroxysmal arrhythmias originating from focal sources variously in both the right and left atria.

None of the cited references discloses a procedure or assembly for creating lesions in cardiac tissue using a light source in cooperation with photoactivatable chemical compounds to form lesions or conduction blocks about focal arrhythmias.

Central to the invention disclosed here is the use of photodynamic therapy (PDT) techniques to create lesions having the same function as those discussed just above. The inventive methods are significantly less invasive; specifically, the lesions may be created without surgery, without the use of any cardiac bypass procedures, and without the use of heat.

Photodynamic Therapy

There are a variety of medical procedures requiring administration of light or irradiated energy to a patient within the body. One such example is the use of a light activated compound selectively to kill target cells in a patient; as noted above, such therapy is often termed photodynamic therapy ("PDT"). In such PDT methods, a light-activated drug is injected into a patient and a targeted light source is used selectively to activate the drug. When activated by light of a proper wavelength, the light-activated drug produces a toxic, often cytotoxic, agent that mediates the destruction of the surrounding cells or tissue.

Currently, the major application of PDT is for the destruction of malignant cell masses. PDT has been used effectively in the treatment of a variety of human tumors and precancerous conditions including basal and squamous cells, skin cancers, breast cancer, metastatic skin cancers, brain tumors, head and neck cancers, stomach cancers, and female genital tract malignancy, cancers and precancerous conditions of the esophagus such as Barrett's esophagus. A review of the history and progress of PDT is provided by Marcus, S. Photodynamic Therapy of Human Cancer: Clinical Status, Potential, and Needs. In Gomer, C. J. (ed.); "Future Directions and Applications in Photodynamic Therapy." Bellingham, W. A. SPIE Optical Engineering Press (1990) pp 5–56. Specific applications of PDT are provided by Overholt et al., Sem. Surg. Oncol. 11:1–5 (1995).

The use of various porphyrin compounds as the photoactivated compounds in such treatments is known. These treatments are often tumor-selective in that selected porphyrin compounds accumulate at higher concentrations in tumor tissue than in normal tissue.

In general, the PDT procedure involves administration of a sensitizer compound (such as the porphyrin derivatives) to the target tissue and a subsequent step involving the application of light to that tissue. The PDT procedures function selectively to eradicate diseased tissue in the immediate area of the light source by generating singlet oxygen and activated molecules which damage tissue in that immediate area. Selectivity is attained through the preferential retention of the photosensitizer in rapidly metabolizing tissue such as tumors (Kessel, David, "Tumor Localization and Photosensitization by Derivatives of Hematoporphyrin. A Review" IEEE J. QUANTUM ELECTRON., QE 23(10): 1718–20 (1987)); virally infected cells (J. Chapman et al, "Inactivation of Viruses in Red Cell Concentrates with the Photo Sensitizer Benzoporphyrin Derivative (BPD)", TRANSFUSION 31(suppl): 47S Abstract S172, (1991) and J. North et al., "Viral Inactivation in Blood and Red Cell Concentrates with Benzoporphyrin Derivative", Blood Cells, 18: 129–140 (1992)); leukaemic cells (C. H. Jamieson, "Preferential Uptake of Benzoporphyrin Derivative by Leukaemic versus Normal Cells", Leuk. Res. (England) 1990, 14 (3), pp 209–210); psoriatic plaque (M. W. Rems et al, "Response of Psoriasis to Red Laser Light (630 nm) Following Systemic Injection of Hematoporphyrin Derivative", Lasers Surg Med. 1984, 4(1) pp 73–77); and atherosclerotic plaque (S. Andersson-Engels et al, "Fluorescence Diagnosis and Photochemical Treatment of Diseased Tissue Using Lasers: Part II", Anal. Chem. 62(1), 19A–27A (1990). The activation of the photosensitizer by light occurs only at the site at which the light is present. Obviously, the photo-sensitizer-mediated destruction of tissue occurs only at the desired treatment site. The non-activated photosensitizer is substantially nontoxic and will eventually be cleared from the body.

In a typical PDT treatment, PHOTOFRIN.RTM. porfimer sodium, BPD, or BPD-MA is injected into a patient. See, for instance, Ho et al., "Activity and Physicochemical Properties of PHOTOFRIN.RTM.", Photochemistry and Photobiology, 54(1), pp 83–87 (1991); U.S. Pat. No. 4,866, 168, to Dougherty et al. An appropriate dose is, e.g., 0.255–2.5 mg/kg of body weight, depending upon the diseased tissue and the choice of photosensitizer. At an appropriate time after photosensitizer administration, the diseased tissue or site is illuminated with a light source at an appropriate wavelength (630 nm for PHOTOFRIN.RTM. and 690 nm for BPD) to activate the photosensitizer. The light-activated drug induces the formation of singlet oxygen and free radicals which damage the surrounding tissue. Both the diseased tissue and the vasculature feeding it are affected and the unwanted tissue is either directly destroyed or starved of oxygen and nutrients due to the occlusion of blood vessels. After the completion of the PDT, the treated tissue becomes necrotic and will either debride naturally or be debrided by the clinician.

Hematoporphyrin and PHOTOFRIN.RTM. have absorption spectra in the neighborhood of 630 nm. The absorption spectra of much blood and tissue is also in the same general spectral region. Consequently, much of the energy impinging upon the treated tissue is absorbed in the tissue itself, thereby limiting, in a practical sense, the physical depth to which the PDT treatment using hematoporphyrin and PHOTOFRIN.RTM. may be used. BPD-MA has an absorption spectra with peaks in longer wavelength regions, e.g., 690 nm. These compounds are viewed as improvements to the PDT treatment method in that the tissues do not absorb so much of the light energy and therefore allow increased depth of light penetration.

It has been the desire and the practice in PDT treatment to provide uniform illumination in a chosen treatment area.

Allardice et al., Gastrointestinal Endoscopy 35:548–551 (1989) and Rowland et al, PCT application WO 90/00914, disclose a light delivery system designed for use with PDT. The disclosed system involves a flexible tube having a dilator and a transparent treatment window that defines a treatment area by using opaque end-caps made of stainless steel. A fiber optic element that is connected to a laser and ends in a diffusing tip is used in combination with the dilator to deliver light to a tissue source. Allardice et al suggests that the advantages of this apparatus over the use of balloon-type catheter reside in providing a more uniform distribution of light.

Nseyo et al, Urology 36:398–402 (1990) and Lundahl, U.S. Pat. Nos. 4,998,930 and 5,125,925, disclose a balloon catheter device for providing uniform light radiation to the inner walls of hollow organs. The device is a balloon catheter design having a balloon at one end of the apparatus and an optical fiber ending in a diffusion tip that is inserted into the lumen of the balloon through the catheter. The catheter's centering tube is said to provide a more uniform distribution of the laser light by centering the optical fiber in the inflated balloon. These catheter devices further incorporate optical sensing fibers in the balloon wall to allow measurement of the resulting illumination.

Panjehpour et al, Lasers and Surgery in Medicine 12:631–638 (1992) discloses the use of a centering balloon catheter for esophageal PDT. Panjehpour et al discloses a cylindrical balloon catheter into which a fiber optic probe ending in a light diffuser is inserted.

Overholt et al, Lasers and Surgery in Medicine 14:27–33 (1994) discloses various structures similar to the balloon catheter device described in Panjehpour et al. Overholt et al's includes a black opaque coating on both ends of the balloon to define a 360° treatment window. Overholt et al additionally describes a modified balloon in which one-half of the circumference of the treatment window is rendered opaque to light using the black coating material. This configuration provides a 180° treatment window.

Rowland et al, PCT application WO 90/00420, discloses a light-delivery system for irradiating a surface. The device has a hemispherical shell in which the inside is entirely coated with a diffuse reflector. A light source is mounted within the shell. The light source may contain a diffusing source at the tip allowing diffusion of light within the reflective shell.

U.S. Pat. No. 5,344,419, to Spears, discloses devices and methods for making laser-balloon catheters. Spears uses a process that etches an end of a fiber optic cable to provide a diffusion tip on that optical cable. The optical cable containing the etched tip is secured within a central channel of a balloon catheter using a coating of adhesive containing microballoons. The position of the tip within the central channel and the microballoons contained in the adhesive provide increased efficiency in diffusing the laser radiation in a cylindrical pattern, providing uniform illumination at the target site.

U.S. Pat. No. 5,354,293, to Beyer et al, discloses a balloon catheter for delivering light for use in PDT. That balloon catheter employs a conical tipped fiber optic cable for deflecting a light beam radially outward through a transparent portion of an inflated balloon.

Although various of the disclosures discussed above provide ways for providing light to a target site, none of them suggest a procedure for creating lesions in cardiac tissue using PDT, particularly for control of cardiac arrhythymia, nor do they suggest endovascular light-delivery devices that are specifically configured to provide limited lineal or circumferential lesions in cardiac tissue.

SUMMARY OF THE INVENTION

This invention relates to methods for producing lesions in cardiac tissue by the step of subjecting cardiac tissue containing a photodynamic drug to a light source in a predetermined pattern to form a lesion corresponding to that predetermined pattern. Normally, the step of forming the lesions is heat-free. The method may also include the step of introducing the photodynamic drug, locally or systemically, to the cardiac tissue.

Preferably the selected, predetermined pattern is one which limits, controls, or prevents cardiac arrhythymia. Among the preferred predetermined patterns are those which encircle the pulmonary vein bed in the left atrium and those which encircle at least one os of superior pulmonary veins in the left atrium.

The procedure may apply the lesions to the cardiac tissue from the exterior of the heart, e.g., through the epicardium or via a surgical or an endovascular procedure to the interior of the heart.

The preferred light delivery device, i.e., for providing light to the selected cardiac tissue, comprises a generally linear member having a distal region with an axis. That distal region preferably includes a substantially clear and linear light emitting region corresponding to said axis. The light emitting region is preferably bendable to conform to curved cardiac tissue. That light emitting region generally emits all of the light emanating from said device and may be, e.g., a window or lens or at least one LED.

DETAILED DESCRIPTION OF THE INVENTION

Figure 1:
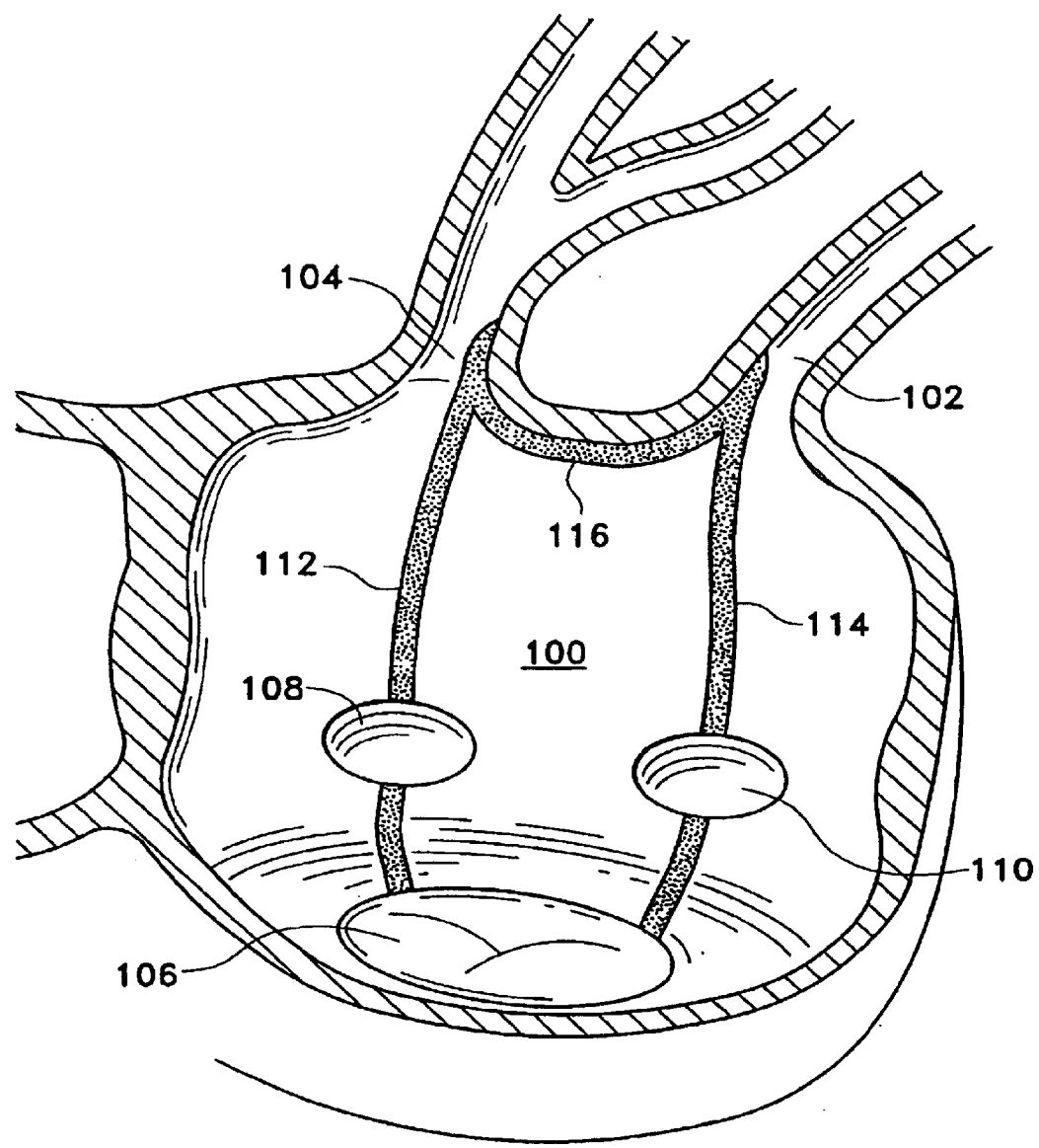
FIG. 1 shows a cutaway of the left atrium of a human heart and the lesion path created in the "maze" procedure as produced by the inventive procedure.

As noted above, many of the currently available ablation techniques use heat to create a lesion in cardiac tissue. Further, since many of the known techniques are quite invasive, the normal but substantial risks associated with heart surgery and the allied equipment are also present. In any case, the heat typically used to produce the lesions is generated by RF current, ultrasound, laser, or microwaves. The generation of heat has the potential to damage non-target tissues and to cause blood coagulation that sometimes results in embolic events. Such embolic events are particularly dangerous when ablating cardiac tissue on the left side of the heart because of the potential for embolic stroke. This invention uses a combination of a photodynamic drug, often systemically administered, and the application of light to the chosen cardiac tissue to create a lesion in that cardiac tissue without using heat. The lesion is a region of tissue that due to the inventive process no longer has significant electrophysiological activity. The lesion does not conduct the cardiac pulse and acts as a block to the fibrillating waves. Therefore, a properly constructed set of lesions terminates fibrillation and makes it highly unlikely that the atria will sustain a fibrillation.

By "photodynamic drug" is meant a photosensitizer that absorbs light over a range of frequencies and produces a chemical reaction, preferably one producing a toxin or other actor capable of creating the desired lesion. Examples of these photodynamic drugs and their sources include: BOPP (boronated porphyrin) from Pacific Pharmaceutical, FOSCAN from Scotia QuantaNova, PHOTOFRIN (dihematoporphyrin ether also known as DHE) from QLT PhotoTherapeutic, and ANTRIN from Pharrnacyclic. For many photosensitizers the wavelength of light used for sensitization is in the range of 405 to 630 nm. The photodynamic effect is stronger at shorter wavelengths, but longer wavelengths penetrate tissue more effectively, so light near 630 nm is preferred. The choice of wavelength is also dependent upon the choice of specific photosensitizers. The light may be from a white light source (e.g. a xenon lamp), from lasers (preferably an argon dye laser), or from LEDs. When the light is absorbed by a photosensitizer, it produces an unstable energy state that ultimately results in the generation of an excited singlet oxygen. An excited singlet oxygen is chemically highly reactive and is toxic to tissue.

In the inventive procedure, a patient is given the photodynamic drug prior to the ablation or lesion-producing step. During the procedure, a catheter or other device containing a light source, or light guides (e.g., using fiber optics) connected to a light source, is placed on the exterior or in the interior of the heart in the area that the physician desires a lesion. The chosen region of the heart is then illuminated with this high intensity light, triggering the photodynamic reaction in the localized area where the lesion is desired. The lesion is created without the generation of heat, and preferably the light is shielded from non-target tissues. As a result the ablation or lesion-producing procedure is safer than current techniques.

The inventive procedure may be used in a variety of ways; the light may be introduced onto the cardiac tissue either from points exterior to the heart or from the interior to the heart. The use of the inventive process allows the creation of fairly deep lesions extending from the epicardium to the endocardium without damaging delicate vessels. In contrast, one major drawback of RF ablation is that since it primarily heats the surface under a current carrying electrode, it is not possible to create deep lesions from the epicardium beneath blood vessels without damaging those vessels.

The patient is first treated, e.g., by intravenous injection or local administration, with a dose of a photodynamic drug. The drug remains inactive until it is activated by a light source.

This choice of a specific photosensitizing drug is not central to this invention; the chosen drug is used in combination with a device to deliver light to the heart to create a lesion, primarily to control or to abolish cardiac arrhythmias of any sort. If the photosensitizer is given systemically, the patient generally must avoid direct sunlight for a period of time after such administration. To avoid or to lessen the impact of this side effect, the photosensitizer may be applied topically or locally to the area of the heart which is to be ablated. This may be done using a separate device from the light delivery device, or in the preferred embodiment, the photosensitizer is incorporated in the light delivery device.

In one variation of the inventive procedure, the primary arrhythmia to be cured is atrial fibrillation. FIG. 1 shows a partial cross-section of a left atrium (100) of a human heart. The superior pulmonary veins (102, 104), the mitral valve annulus (106), and the inferior pulmonary veins (108, 110) are also depicted. FIG. 1 also shows the "maze" procedure discussed in the Cox article discussed above is depicted using the procedure of the invention. Specifically created are: a lesion (112) extending from the os of the superior pulmonary vein (104) by the os of the inferior pulmonary vein (108) and to the mitral valve annulus (106), a second lesion (114) extending from the os of the superior pulmonary vein (102) by the os of the inferior pulmonary vein (110) and to the mitral valve annulus (106), and a third lesion (116) between the os of the two superior pulmonary veins (102, 104).

Figure 2:
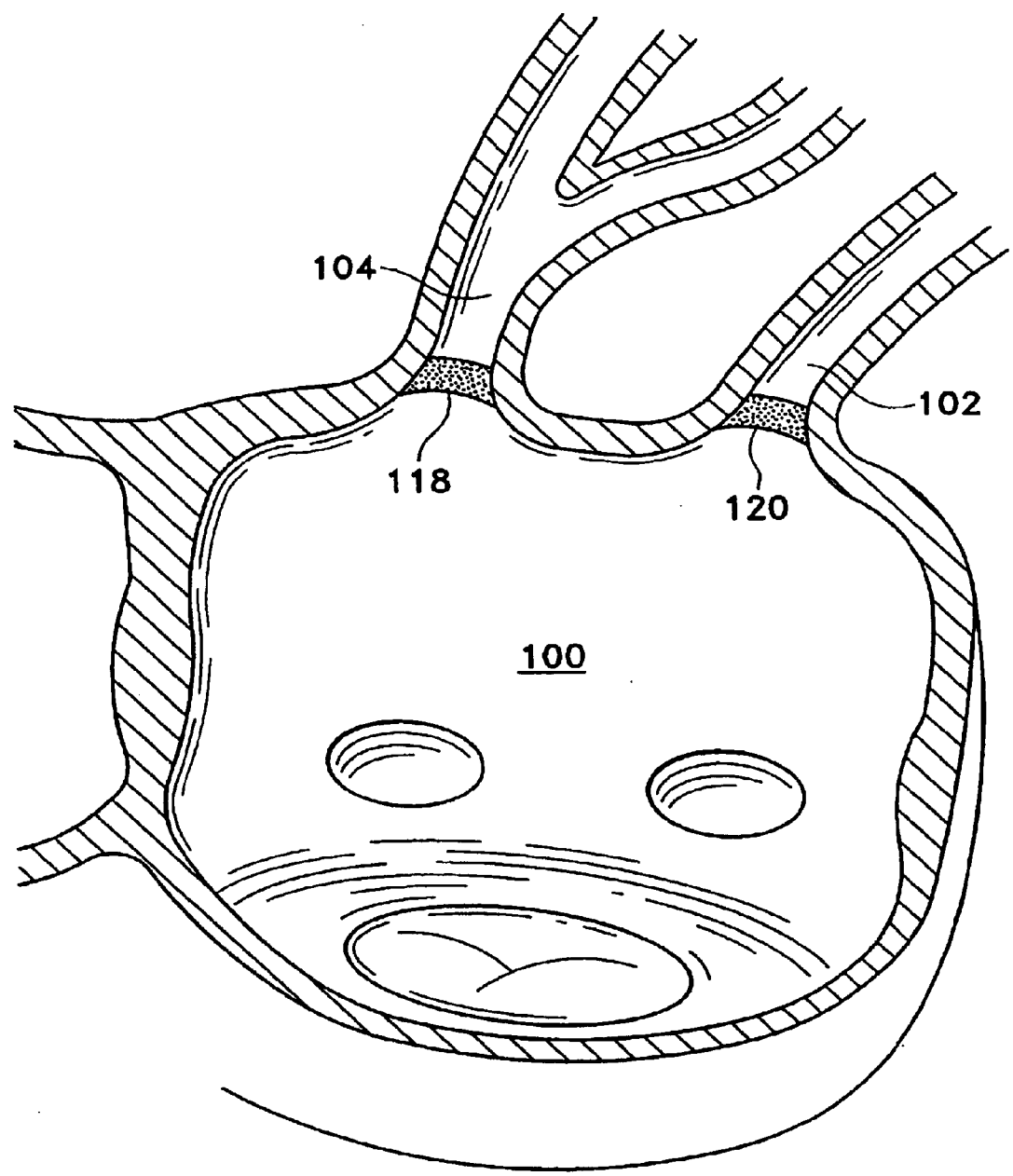
FIG. 2 also shows a cutaway of the left atrium of a human heart and the circumferential lesion path created in the os of the superior pulmonary veins as produced by the inventive procedure.

FIG. 2 shows the same view of the heart as found in FIG. 1, the difference being the circumferential lesions (118, 120) created using the inventive procedure respectively in the os of the superior pulmonary veins (104, 102). This procedure is explained with greater particularity in U.S. Pat. No. 6,024,740, to Lesh et al, at least when performed with RF as the ablation energy.

Again, it should be understood that once the photosensitizing chemical is applied to the cardiac region to be at which a lesion is to be formed, the light may be introduced either from the interior or exterior of the heart. This is especially true in treating atrial fibrillation where the typical ectopic arrhythmic foci are accessible from the exterior. The application of light may be via an endovascular catheter, an endoscopic device, or by a device applied by hand or robot through a surgical opening.

Figure 3A:
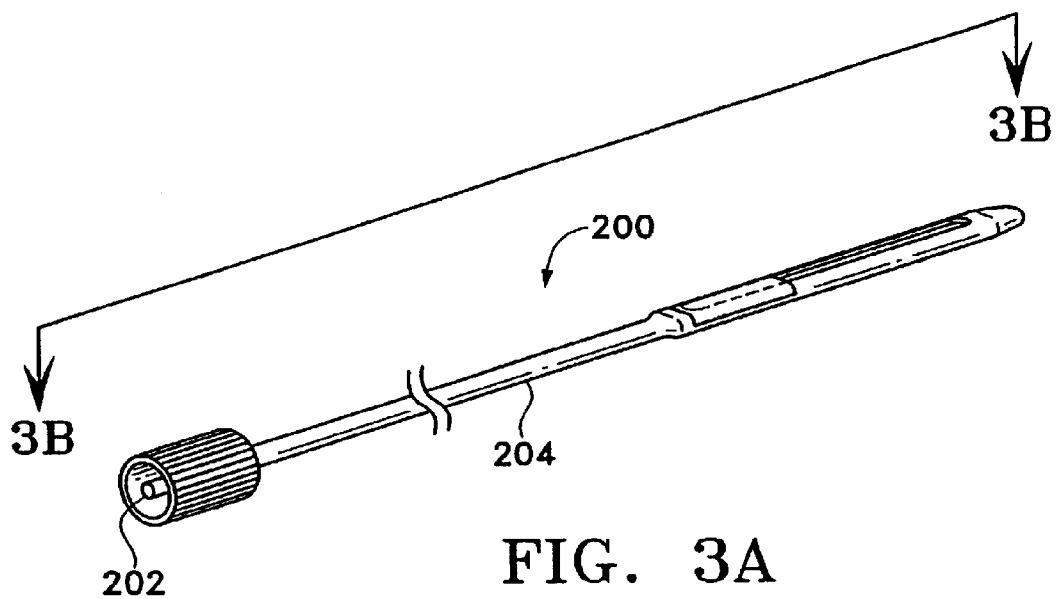
FIGS. 3A and 3B show respectively side and top views of a light application device in accord with this invention.
Figure 3B:
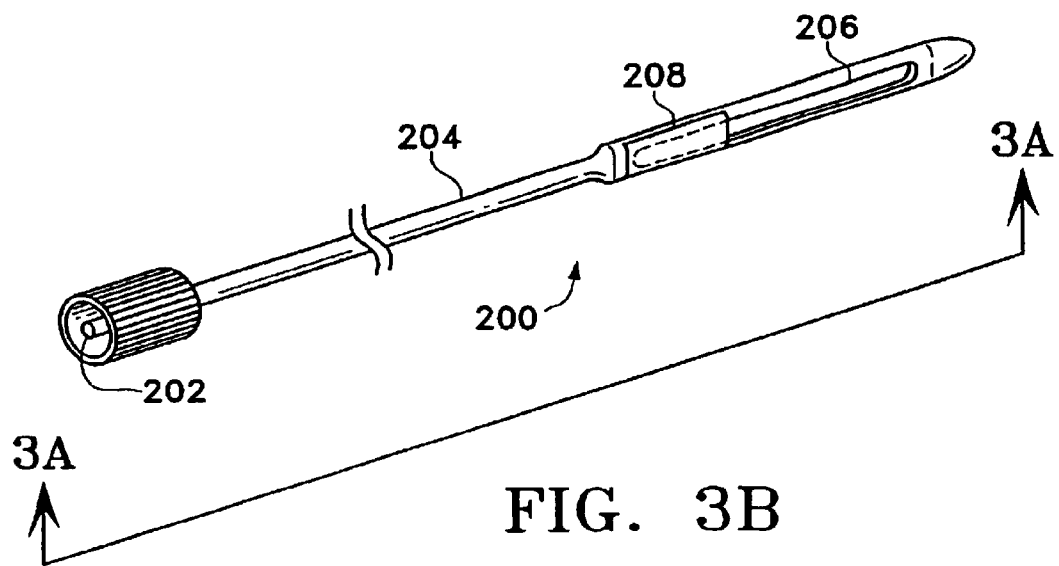

FIGS. 3A and 3B show side and top views of a device (200) to deliver light from a light source to the epicardium of the heart. A proximal port (202) on the device interfaces with an external light source. The light source may be, for instance, a xenon lamp, a high intensity LED source, laser, or any other source capable of producing illumination in the appropriate wavelengths, e.g., from 350 to 700 nm. Fiber optics or other light guides extend inside a flexible housing (204) typically made of a polymeric material, to carry the light from the port (202) to the distal end of the device. At the distal end, the light guide terminates in an elongated, generally linear window (or lens) (206) that allows the light to escape onto the heart surface. The back side of the window is opaque to ensure that no light escapes to reach tissues other than those targeted by the physician. To modify the area of tissue that is illuminated, the window (206) may obviously be manufactured in different sizes or may be shuttered by the application of an opaque adhesive tape (208) or other material.

In the alternative, the device (200) may be configured so that individual strands of the fibers in the fiber optic cable are tied to individual portions of the window (206). Some portion of the proximal ends of the individual fibers in the fiber optic cable available at the proximal connector (202), may be selectively blocked from the light source to cause less of the window (206) to be illuminated.

Figure 4A:
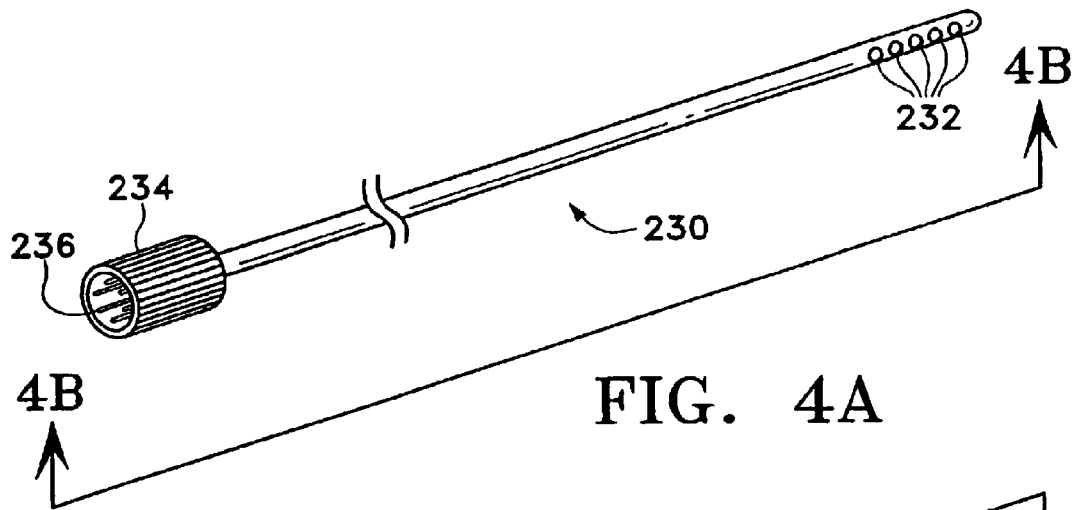
FIGS. 4A and 4B show respectively top and side views of a light application device using LED's made according to the invention.
Figure 4B:
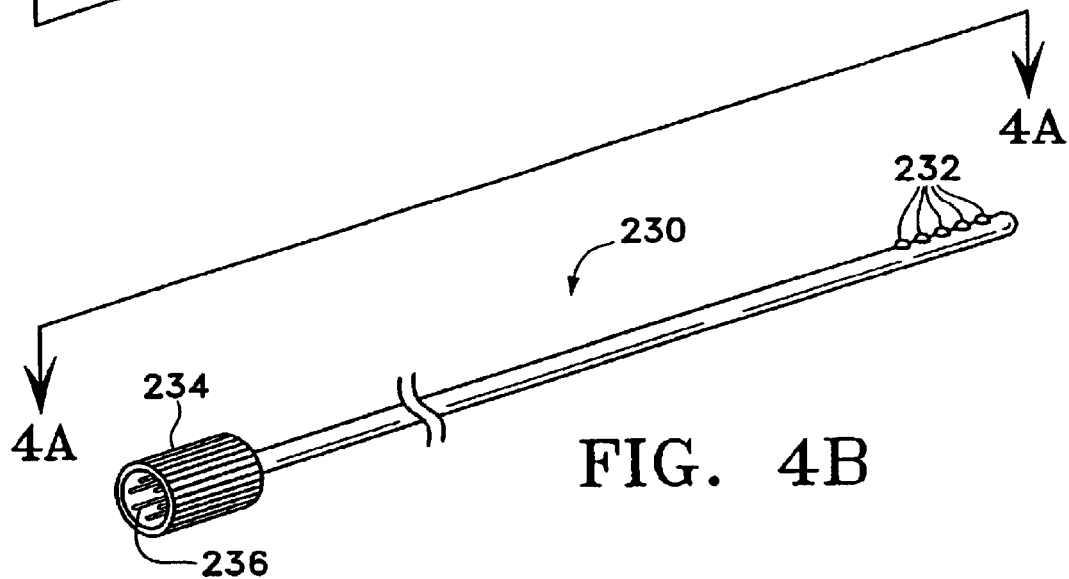

FIGS. 4A and 4B show top and side views of a device (230) having light emitting devices (generally light emitting diodes or LED's) (232) on the distal end, that deliver light, e.g., to the epicardium of the heart. The proximal connector (234) connects to the light emitting devices (232) through electrical conductors (236). The light emitting devices (232) are preferably light emitting diodes (LED's) that emit light around 600 nanometers which penetrates tissue well. Again, the back side of the device is opaque to assure that only tissues that are targeted for ablation receive light.

Figure 5:
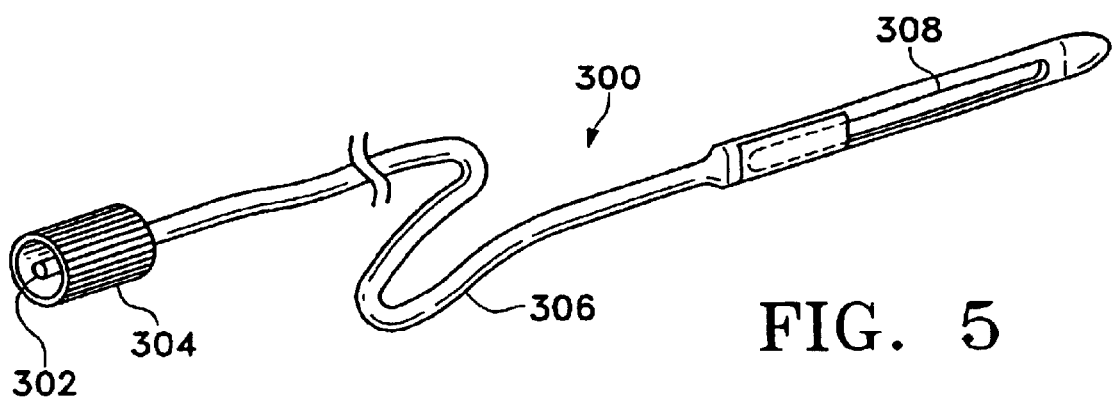
FIG. 5 shows a plan view of a light application catheter made according to the invention.

For some cardiac procedures, a device that delivers light to the inside of the heart (endocardially) is preferred. FIG. 5 shows a catheter-based device (300) configured to introduce light into the heart to activate a photosensitizing drug. The proximal connector (302) is adapted to connect to an external light source. Fiber optics or other light guides (304) carry the light through the flexible catheter body (306) to the clear distal window (308). The back side of the window is opaque to assure that only tissues that are intended for ablation receive light. Design of the catheter body to provide close contact between the distal window or lens (308) with the interior heart wall to produce a narrow and clean-edged lesion is within the scope of the ordinary catheter designed in the art. The distal window (308) may also be a spot rather than a linear window and moved along the cardiac tissue at an appropriate rate to produce a lesion. Suitable lesion patterns for controlling atrial fibrillation are depicted in FIGS. 1 and 2.

Again, methods of controlling atrial fibrillation include creation of a lesion either encircling the pulmonary vein bed or around the superior pulmonary arteries in the left atrium.

Figure 6:
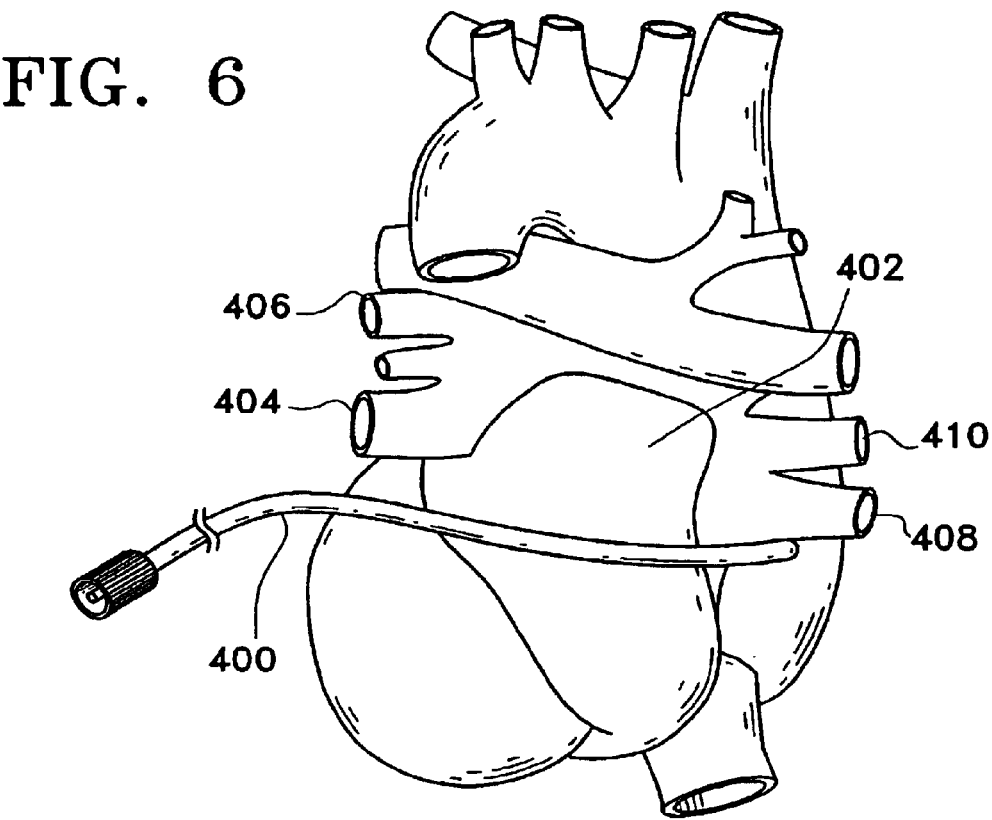
FIG. 6 shows a step in the application of light through the epicardium in creating lesions for one predetermined pattern for alleviating arrhythmia.

FIG. 6 shows the device of variously of FIGS. 2A, 2B, 3A, or 3B in one position producing a first portion of a lesion around the pulmonary vein bed. The procedure involves placement of the light-emitting device (400) along the left atrium (402) between the left inferior (404) and superior (406) pulmonary veins and the right inferior (408) and superior (410) pulmonary veins. The device may be placed encircling the vein bed or, as shown, be sequentially placed eventually to encircle the veins.

Figure 7:
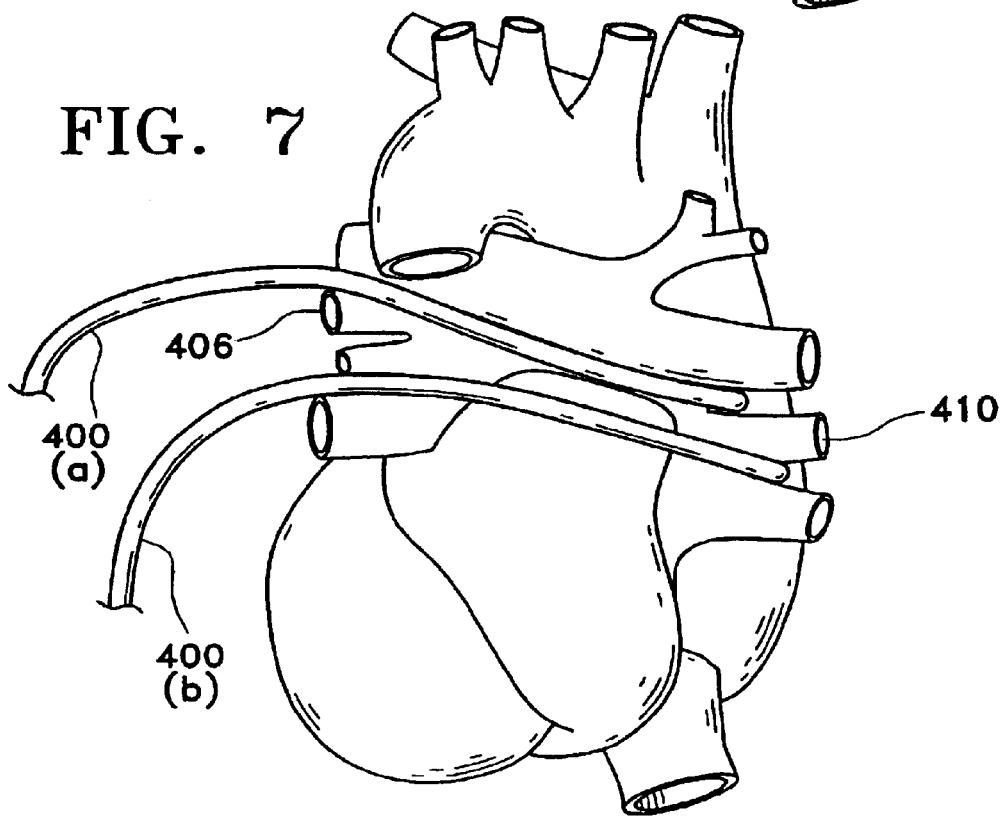
FIG. 7 shows a step in the application of light through the epicardium in creating lesions for a second predetermined pattern for alleviating arrhythmia.

Similarly, FIG. 7 shows the placement of the device (400) of variously of FIGS. 2A, 2B, 3A, or 3B in two positions (400(a)) and (400(b)) on the epicardium, each producing portions of a lesion encircling the bases of the superior pulmonary veins (406, 410) in a procedure analogous to that discussed in Lesh et al above.

I claim as my invention:

1. A method for producing predetermined patterned lesions in cardiac tissue comprising the step of subjecting cardiac tissue containing a photodynamic drug to a light source, the light source arranged so as to produce a lesion in a pattern corresponding to the light source such that non-target tissue is not exposed to the light.

2. The method of claim 1 further comprising the step of introducing said photodynamic drug to said cardiac tissue.

3. The method of claim 2 wherein said introducing step comprises systemic introduction of said photodynamic drug to a patient having said cardiac tissue.

4. The method of claim 2 wherein said introducing step comprises local introduction of said photodynamic drug to said cardiac tissue.

5. The method of claim 1 wherein said predetermined pattern encircles an ectopic arrhythmic focus in said cardiac tissue.

6. The method of claim 1 wherein said predetermined pattern encircles the pulmonary vein bed in the left atrium of a patient having said cardiac tissue.

7. The method of claim 1 wherein said predetermined pattern encircles at least one os of superior pulmonary veins in the left atrium of a patient having said cardiac tissue.

8. The method of claim 1 wherein said predetermined pattern is exterior to a heart containing said cardiac tissue.

9. The method of claim 8 wherein said light delivery is through an epicardium.

10. The method of claim 1 wherein said predetermined pattern is interior to a heart containing said cardiac tissue.

11. A method for the heat-free treatment of a selected cardiac tissue comprising the step of subjecting said cardiac tissue containing a photodynamic drug to a light source, the light source arranged so as to produce a lesion in a predetermined pattern corresponding to the light source such that non-target tissue is not exposed to the light.

12. The method of claim 11 further comprising the step of introducing said photodynamic drug to said cardiac tissue.

13. The method of claim 12 wherein said introducing step comprises systemic introduction of said photodynamic drug to a patient having said cardiac tissue.

14. The method of claim 12 wherein said introducing step comprises local introduction of said photodynamic drug to said cardiac tissue.

15. The method of claim 11 wherein said predetermined pattern encircles an ectopic arrhythmic focus in said cardiac tissue.

16. The method of claim 11 wherein said predetermined pattern encircles the pulmonary vein bed in the left atrium of a patient having said cardiac tissue.

17. The method of claim 11 wherein said predetermined pattern encircles at least one os of superior pulmonary veins in the left atrium of a patient having said cardiac tissue.

18. The method of claim 11 wherein said predetermined pattern is exterior to a heart containing said cardiac tissue.

19. The method of claim 11 wherein said step of subjecting said cardiac tissue containing a photodynamic drug to a light source to form a lesion comprises delivering said light through an epicardium.

20. The method of claim 11 wherein said step of subjecting said cardiac tissue containing a photodynamic drug to a light source to form a lesion comprises delivering said light interior to a heart containing said cardiac tissue.

21. A light delivery device for providing light to a cardiac tissue comprising a generally linear member having a distal region, said distal region comprising an axis, and a transparent linear light emitting region corresponding to the axis, the linear light emitting region being surrounded by a substantially opaque region on each of its surfaces but its light emitting surface, wherein a portion of the linear light emitting region can be selectively illuminated, the light emitting region emitting substantially all light emanating from the device to produce a lesion in a pattern corresponding to the light emitted from the light emitting region, the linear light emitting region further being conformable to a curved cardiac tissue.

22. The light delivery device of claim 21 wherein said light emitting region comprises a window or lens.

23. The light delivery device of claim 21 wherein said light emitting region comprises at least one LED.

\* \* \* \* \*